US008465347B2

(12) United States Patent
 Hart

(10) Patent No.: US 8,465,347 B2
(45) Date of Patent: Jun. 18, 2013

(54) RETRACTABLE WATER DISPENSER ARM FOR GRINDER/POLISHER

(75) Inventor: Michael F. Hart, Mundelein, IL (US)

(73) Assignee: Illinois Tool Works Inc., Glenview, IL (US)

( * ) Notice: Subject to any disclaimer, the term of this patent is extended or adjusted under 35 U.S.C. 154(b) by 877 days.

(21) Appl. No.: 12/501,623

(22) Filed: Jul. 13, 2009

(65) Prior Publication Data

US 2010/0062696 A1 Mar. 11, 2010

Related U.S. Application Data

(60) Provisional application No. 61/096,048, filed on Sep. 11, 2008.

(51) Int. Cl.
 *B24B 21/18* (2006.01)
(52) U.S. Cl.
 USPC .... 451/444; 433/78; 137/355.16; 137/355.23
(58) Field of Classification Search
 USPC ............. 451/60, 285, 287, 444, 446; 433/78; 137/355.16, 355.2, 355.23, 355.24
 See application file for complete search history.

(56) References Cited

U.S. PATENT DOCUMENTS

| 1,642,132 | A | | 9/1927 | Walter |
| 2,896,659 | A | * | 7/1959 | Erickson ................. 137/355.21 |
| 4,114,273 | A | * | 9/1978 | McGaha ........................ 433/27 |
| 4,557,436 | A | | 12/1985 | Drake |
| 6,334,457 | B1 | | 1/2002 | Baker, IV |
| 6,381,774 | B1 | * | 5/2002 | Wales ............................... 4/678 |
| 6,623,341 | B2 | * | 9/2003 | Tolles .......................... 451/288 |
| 6,749,135 | B2 | | 6/2004 | Groblebe et al. |

FOREIGN PATENT DOCUMENTS

CN 2930883 8/2007

OTHER PUBLICATIONS

International Search Report for PCT/US09/052199 dated Sep. 22, 2009.

* cited by examiner

*Primary Examiner* — Eileen P. Morgan
(74) *Attorney, Agent, or Firm* — Levenfeld Pearlstein, LLC

(57) ABSTRACT

A retractable water dispenser arm system for a grinder/polisher includes a flexible hose formed, in part in a loop and affixed at at least one location to a base of the grinder polisher. A spout is mounted to an end of the flexible hose. A biased tension arm engages the hose at the loop, and is moveable, along with movement of the hose, to maintain the hose in tension. The biased tension arm includes a roller over which the hose traverses. A mount on the base is configured to receive the spout and is further configured for traverse of the hose therethrough. The mount includes a mount roller operably mounted thereto for guiding the hose through the mount.

10 Claims, 4 Drawing Sheets

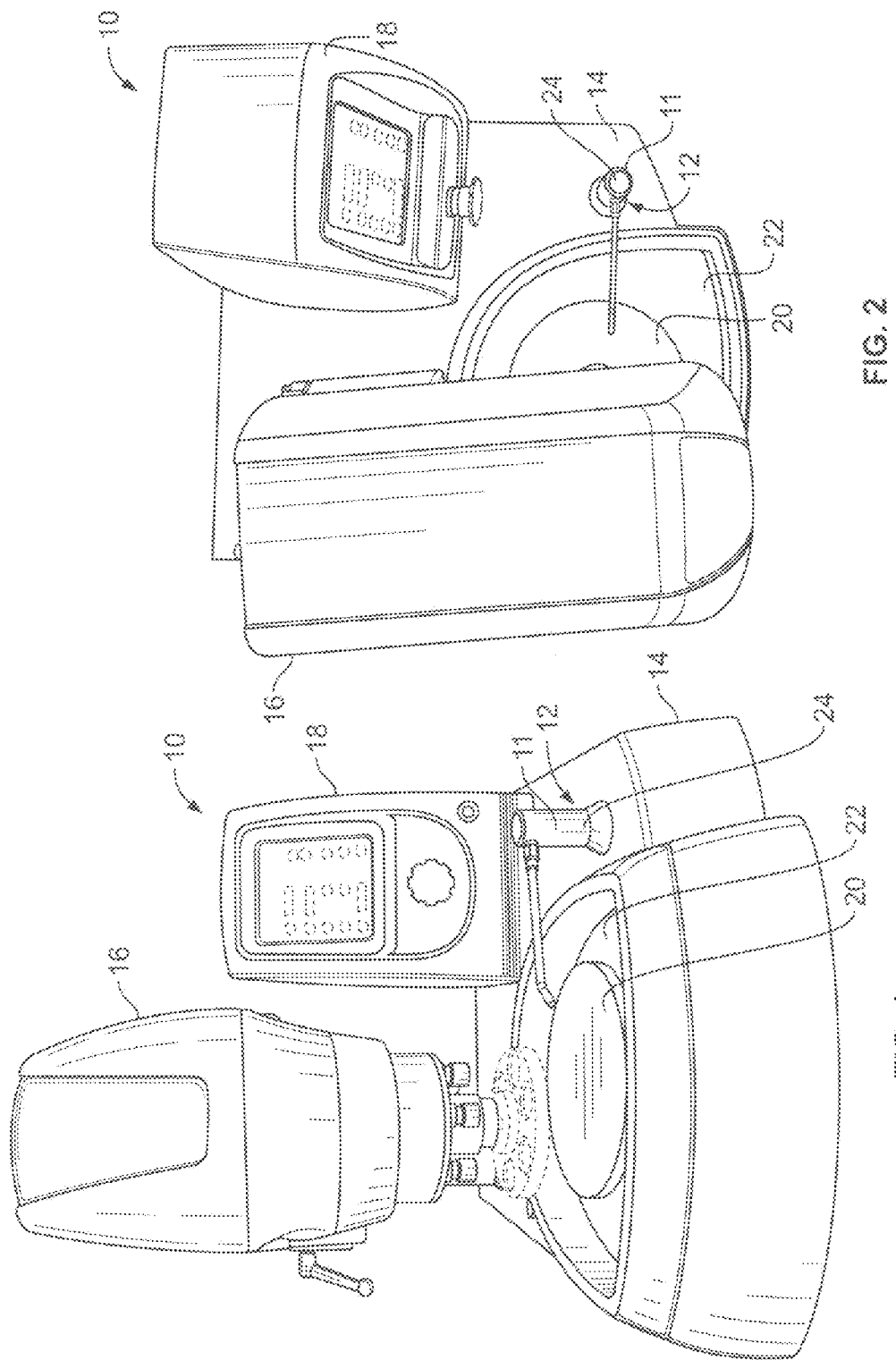

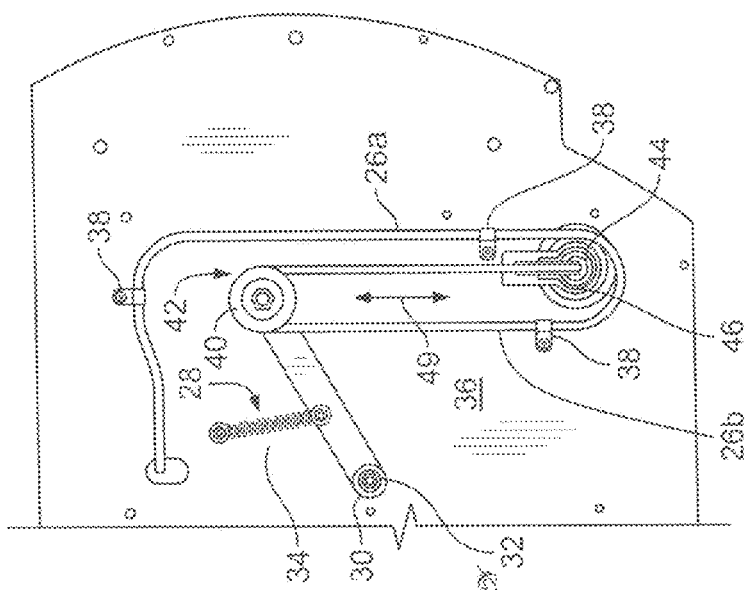
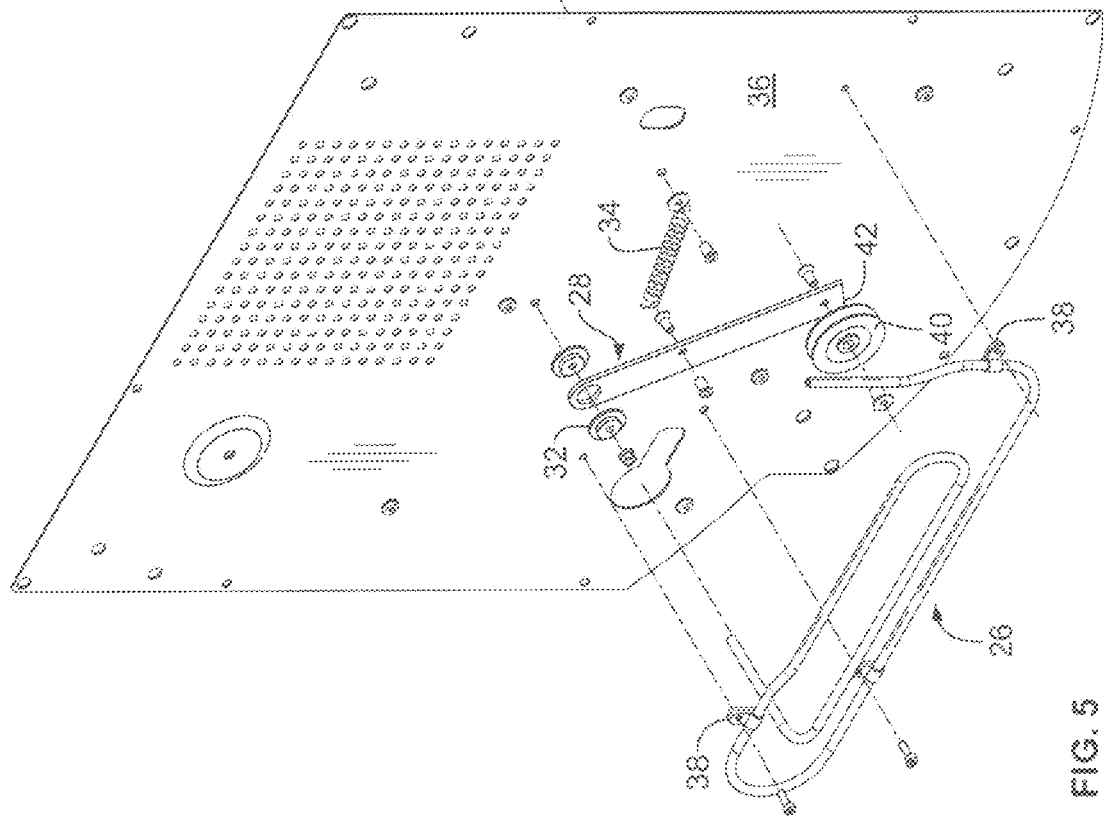

RETRACTABLE WATER DISPENSER ARM FOR GRINDER/POLISHER

CROSS-REFERENCE TO RELATED APPLICATION DATA

This application claims priority to U.S. Provisional Patent Application Ser. No. 61/096,048, filed Sep. 11, 2008.

BACKGROUND OF THE INVENTION

The present invention relates to a grinder/polisher. More particularly, the present invention relates to an improved retractable water dispenser arm for a grinder/polisher.

Grinder/polishers are in use in many industries. They are often used to prepare samples of metals, polymers, ceramics or the like for further examination, such as by microscopic examination.

Grinder/polishers include a sample or specimen holder that is configured to rotate relative to a platen that is also configured to rotate. In this manner, there are two rotating motions occurring simultaneously. A slurry, generally abrasive, is injected onto the platen to provide an abrasive medium for grinding and polishing the specimen.

The platen is supported within a bowl which serves as a repository for debris that is generated during the grinding/polishing operation. Water or another fluid is used to rinse the bowl to clear the debris. It has been found that even with known rinsing systems, debris can collect in the bowl and cause unsightly and inconvenient accumulation in the bowl.

Known water dispensing systems have long, unwieldy hoses and often require that an operator use two hands to properly dispense water. This can be quite cumbersome when the operators hands and attention are required for grinding/polishing the specimen. It can also be cumbersome when trying to thread or push a length of hose back into an opening in the base of the grinder polisher.

Accordingly, there is a need for an improved water dispensing system for a grinder polisher. Desirably, such a dispensing system permits one-handed operation for dispensing water during grinding/polishing operations. More desirably, such a system provides for self storing of the supply hose and prevents inadvertently directing water spray out of the grinder/polisher bowl.

SUMMARY OF THE INVENTION

A retractable water dispenser arm system is for use on a grinder/polisher having a bowl. The dispenser arm includes a flexible hose formed, in part in a loop and affixed at one or more locations to a base of the grinder polisher. The flexible hose defines a fixed portion fixed to the base and an extendable/retractable portion.

A spout is mounted to an end of the extendable/retractable portion.

A biased tension arm is mounted to the base and engages the hose at the loop. The tension arm is moveable, along with movement of the hose, to maintain the hose in tension. The biased tension arm includes a roller, preferably non-abrading, over which the hose traverses. The arm is biased by a spring. The tension arm urges the flexible hose into a retracted state.

A mount is mounted to the base into which the spout rests and through which the hose traverses. The spout and extendable/retractable portion of the hose are retracted from the grinder/polisher and the biased tension arm is biased to retract the spout and extendable/retractable portion back into the grinder/polisher.

A mount roller is operably mounted to the mount for guiding the extendable/retractable portion through the mount. Cooperating movement limiting elements, such as a pin and receiving notch, can be positioned on the spout and the mount to limit rotation of the spout relative to the mount to maintain the spout positioned over the bowl.

The rollers are formed from a non-abrading material, such as a plastic material.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying photographs (Ph.) and drawings (FIG.), wherein:

FIG. 1 is a front view of a grinder/polisher having a retractable water dispensing system arm embodying the principles of the present invention;

FIG. 2 is a top view of the grinder/polisher of FIG. 1;

FIG. 4 is a bottom view of the grinder polisher;

FIG. 5 is an exploded view of the tension arm components and supply hose; and

DETAILED DESCRIPTION OF THE INVENTION

Figure 3:
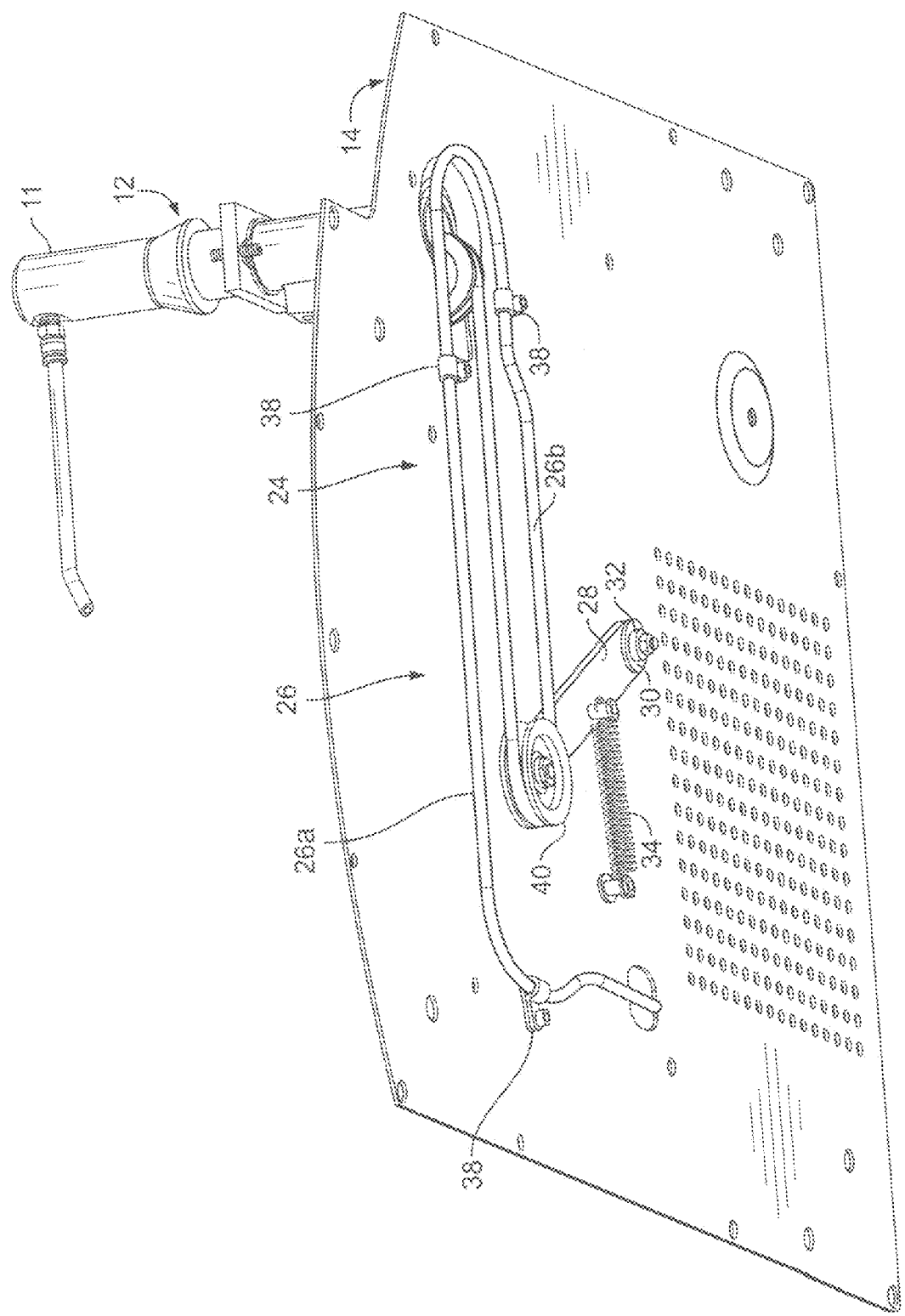
FIG. 3 is a bottom perspective illustration of the grinder/polisher showing the retractable water dispenser system.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Referring now to the figures and in particular, to FIGS. 1-2, there is shown a grinder/polisher 10 having a retractable water dispenser arm system 12 embodying the principles of the present invention. The grinder/polisher 10 includes, generally, a base 14, a head 16 and a control panel 18.

The base 14 houses a rotating platen 20 and a fluid supply and rinse (water dispensing) system. The base 14 also houses a collection bowl or basin 22 in which the fluid is collected, as well as debris that is generated during grinding/polishing.

As will be appreciated, there can be a considerable amount of debris that is generated during operation that must be rinsed away. Accordingly, the water dispensing system 12 is an integral and important part of the overall grinder/polisher 10 system.

Known grinder/polishers have a water dispensing arm that is fed by a hose that is mounted to (fed through) the base. The arm is merely pulled from the base and, when finished, the hose must be threaded back into the base. This can be problematic in that it may require the use of two hands to thread the hose back into the base.

The present system 12 uses a retractable hose assembly 24 that is configured for one-handed operation. The system 12 includes a spout or water dispensing handle 11, and a looped hose (as indicated at 26), a portion of which 26a is fixed to the base 14 and a portion of which (the loop 26b) is configured to flex as it is extended from and retracted back into the base 14 (e.g., an extendable/retractable portion). The flexing portion (the extendable/retractable portion 26b) of the hose 26 is mounted to the base 14 by a spring biased roller arm 28. The roller arm 28 is pivotably mounted to the base 14 at a pivot 30 by one or more bearings 32. The roller arm 28 is configured to retract or take up the slack in the hose 26b when the water dispensing head (spout) 11 is nested in the base 14 (see FIGS. 1 and 2). In this position, which is seen in FIGS. 3 and 4, the spring 34 is in a relaxed state and the "slack" is taken up by extended lengths of hose 26b on the underside 36 of the top surface of the base 14.

In a present system, the fixed hose 26a is fixed to the base 14 at three locations by clips 38, such as the illustrated nylon clips that secure the hose 26a to the base 14. The roller arm 28 includes a roller 40 at the free end 42 thereof on which the looped hose portion 26b is fitted.

Figure 6:
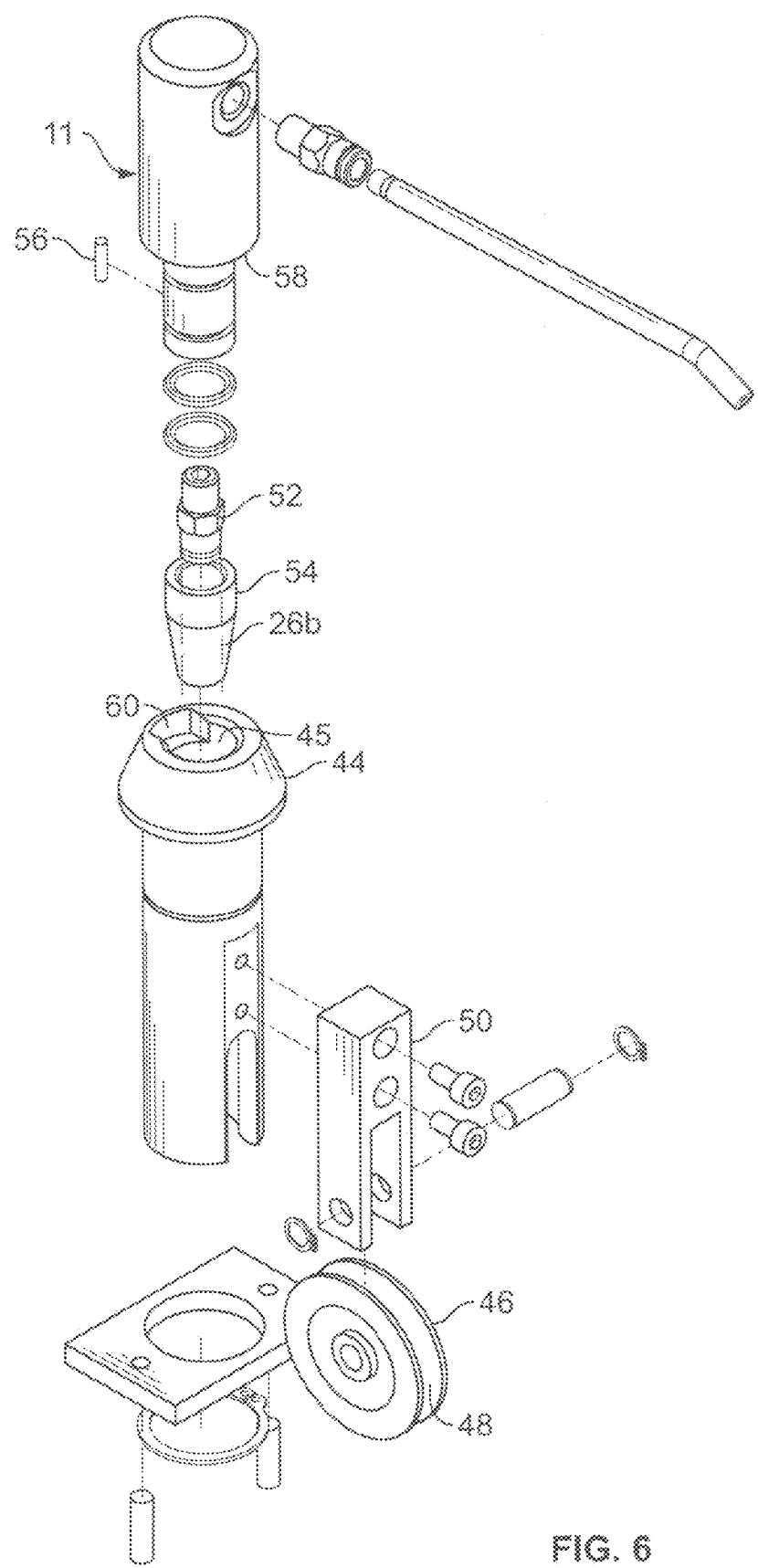
FIG. 6 is an exploded view of the dispenser arm and components.

The dispensing arm system 12 is illustrated in FIGS. 6 and 7. The system 12 includes a spout mount 44 that is mounted to the base 12 and has a bore 45, through which the hose 26b traverses. The spout mount 44 includes a roller 46 that is mounted, in part above the base 14 and in part mounted below the base 14. The roller 46 redirects the hose 26b from under the base 14 to above the base 14. The roller 46 has a channel 48 that is aligned with the bore 45 in the mount 44 to direct the hose 26b through the bore 45. The channel is also aligned with the direction (see arrow at 49) that the hose 26b moves under the base 14; the channel 48 is also aligned with an upward direction from the base 14 (the direction in which the hose 26b is "pulled" from the base 14).

The roller 46 is mounted to the spout mount 44 by a roller mount 50 that is affixed to the spout mount 44. The roller 46 provides a smooth path for the hose 26b as it moves through the spout mount 44 (through the base 14), and maintains the hose 26b away from edges or other surfaces/elements that might otherwise interfere with unfettered movement of the hose 26b. The roller 46 also prevents chaffing or abrasion of the hose 26b. Preferably, the rollers 40, 46 are formed from a non-abrading material, such as a smooth, non-abrading plastic material.

The hose 26b is mounted to the spout 11 (that part that is extended from and retracted into the base 14) by a fitting 52. The fitting 52, which is preferably a quick-connect type fitting, is positioned under a cone 54. The cone 54 provides protection for the hose 26b connection as it is pulled from and inserted into the spout mount 44. In that the cone 54 is positioned over the fitting 52, it also prevents inadvertently disconnecting the fitting 52 (e.g., inadvertently disconnecting the hose 26b) from the arm system 12.

The spout 11 also includes a locating pin 56 that is mounted to the bottom 58 of the spout 11 and is configured to rest in a slot or notch 60 in the mount 44. The pin 56 permits some movement (e.g., rotation) of the spout 11 in the mount 44, but prevents over-rotation, thus preventing the spout 11 from being rotated to a position outside of the bowl 22. In this manner, the cooperating elements (the pin 56 and slot or notch 60) maintain the spout 11 over the bowl 22 to prevent the spout from being rotated such that water is dispensed outside of the bowl 22 when the spout 11 is resting in the mount 44.

It will be appreciated that the present retractable water dispensing system 12 provides a number of advantages over known hose systems. First, the tensioned roller arm 28 prevents the hose 26b from becoming tangled and returns the hose 26b to a "safe" location within grinder/polisher base 14. It also takes up any slack in the hose 26b and precludes having to push the hose back into an opening in the base. This allows for one-handed operation and sure and positive re-seating of the spout 11 in the grinder/polisher base 14.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the invention.

What is claimed is:

1. A retractable water dispenser arm system for a grinder/polisher, the grinder/polisher having a bowl, the water dispenser arm comprising:
    a flexible hose formed, in part in a loop and affixed at at least one location to a base of the grinder polisher, the flexible hose defining a fixed portion and an extendable/retractable portion;
    a spout mounted to an end of the extendable/retractable portion;
    a biased tension arm engaging the hose at the loop, the biased tension arm moveable, along with movement of the hose, to maintain the hose in tension, the biased tension arm including a roller over which the hose traverses, the biased tension arm urging the flexible hose into a retracted state;
    a mount into which the spout rests and through which the hose traverses; and
    cooperating movement limiting elements on the spout and the mount to limit rotation of the spout relative to the mount,
    wherein the spout and extendable/retractable portion of the hose are retracted from the grinder/polisher and wherein the biased tension arm is biased to and retracts the spout and extendable/retractable portion back into the grinder/polisher.

2. The retractable water dispenser arm in accordance with claim 1 including a mount roller operably mounted to the mount for guiding the extendable/retractable portion through the mount.

3. The retractable water dispenser arm in accordance with claim 1 including a biasing element for biasing the biased tension arm.

4. The retractable water dispenser arm in accordance with claim 3 wherein the biasing element is a spring mounted at one end to the biased tension arm and at an opposite end to the grinder/polisher.

5. The retractable water dispenser arm in accordance with claim 1 wherein the cooperating movement limiting elements include a pin disposed in the spout and a notch disposed in the mount to maintain the spout positioned over the bowl.

6. The retractable water dispenser arm in accordance with claim 1 wherein the fixed portion is maintained fixed by a plurality of mounting elements secured to the grinder/polisher.

7. The retractable water dispenser arm in accordance with claim 6 wherein the mounting elements are clips.

8. The retractable water dispenser arm in accordance with claim 2 wherein the mount roller includes a channel therein to direct the extendable/retractable portion through a bore in the mount.

9. The retractable water dispenser arm in accordance with claim 2 wherein the biased tension arm roller and the mount roller are formed from a non-abrading material.

10. The retractable water dispenser arm in accordance with claim 9 wherein the non-abrading material is a plastic.

* * * * *